United States Patent
Hadzic et al.

(10) Patent No.: US 6,866,648 B2
(45) Date of Patent: Mar. 15, 2005

(54) METHOD AND APPARATUS TO DECREASE THE RISK OF INTRANEURONAL INJECTION DURING ADMINISTRATION OF NERVE BLOCK ANESTHESIA

(75) Inventors: Admir Hadzic, Montclair, NJ (US); Jerry D. Vloka, Upper Saddle River, NJ (US); Sergio Giglioli, Mirandola (IT)

(73) Assignee: Macosta Medical U.S.A., L.L.C., Houston, TX (US)

( * ) Notice: Subject to any disclaimer, the term of this patent is extended or adjusted under 35 U.S.C. 154(b) by 0 days.

(21) Appl. No.: 10/156,416

(22) Filed: May 28, 2002

(65) Prior Publication Data

US 2003/0225371 A1 Dec. 4, 2003

(51) Int. Cl.⁷ .................. A61M 31/00; A61M 25/00
(52) U.S. Cl. ..................... 604/93.01; 604/512
(58) Field of Search ............... 604/65.67, 506, 604/507, 272

(56) References Cited

U.S. PATENT DOCUMENTS

| | | | | |
|---|---|---|---|---|
| 4,282,881 A | * | 8/1981 | Todd et al. | 600/487 |
| 4,606,391 A | | 8/1986 | Achterholt | |
| 4,759,750 A | * | 7/1988 | DeVries et al. | 604/121 |
| 4,775,367 A | | 10/1988 | Schmidt | |
| 4,889,529 A | | 12/1989 | Haindl | |
| 4,917,668 A | | 4/1990 | Haindl | |
| 4,917,670 A | | 4/1990 | Hurley et al. | |
| 4,929,238 A | * | 5/1990 | Baum | 604/208 |
| 4,950,233 A | * | 8/1990 | Abramowitz | 604/512 |
| 4,994,035 A | * | 2/1991 | Mokros | 604/118 |
| 4,994,036 A | | 2/1991 | Biscoping et al. | |
| 5,007,365 A | | 4/1991 | Hwang | |
| 5,085,631 A | | 2/1992 | Leighton | |
| 5,106,376 A | | 4/1992 | Mononen et al. | |
| 5,119,832 A | | 6/1992 | Xavier | |
| 5,135,525 A | | 8/1992 | Biscoping et al. | |
| 5,295,967 A | * | 3/1994 | Rondelet et al. | 604/154 |
| 5,312,374 A | | 5/1994 | Gurmarnik | |
| 5,328,479 A | | 7/1994 | Gurmarnik | |
| 5,378,241 A | | 1/1995 | Haindl | |
| 5,512,052 A | | 4/1996 | Jesch | |
| 5,630,802 A | | 5/1997 | Moellmann et al. | |
| 6,086,559 A | | 7/2000 | Enk | |
| 6,113,574 A | * | 9/2000 | Spinello | 604/131 |
| 6,200,289 B1 | * | 3/2001 | Hochman et al. | 604/67 |

OTHER PUBLICATIONS

D. Selander et al., Paresthesiae or No Paresthesiae, Acta anaesth. scand. 23:27–33 (1979).

Y. Auroy et al., Serious Complications Related to Regional Anesthesia, Anethesiology, 87:479–486 (1997).

T. Stan et al., The Incidence of Neurovascular Complications Following Axillary Brachial Plexus Block Using a Transarterial Approach, Regional Anesthesia, 20:486–492 (1995).

(List continued on next page.)

*Primary Examiner*—Michael J. Hayes
(74) *Attorney, Agent, or Firm*—Fitch, Even, Tabin & Flannery (57) ABSTRACT

An objective and reproducible system for, and method of, monitoring and/or controlling the pressure during nerve blockage injection, especially by less experienced personnel, is provided in order to decrease the possibility of intraneuronal injection. More specifically, the present invention employs a pressure sensing and/or limiting device located between an injection device (typically a syringe) and a nerve block needle whereby injection pressure during a nerve block injection can be easily and objectively monitored, thereby allowing the operator to monitor the injection pressure and/or injection speed during a nerve blockage injection procedure and to take appropriate corrective actions if abnormal pressure conditions are observed.

12 Claims, 3 Drawing Sheets

OTHER PUBLICATIONS

D. Selander et al., Longitudinal Spread of Intraneurally Injected Local Anesthetics, Acta anaesth. scand. 22:622–634 (1978).

R. Stark, Neurologic Injury From Axillary Block Anesthesia, The Journal of Hand Surgery, 21A:391–396 (1996).

T. Stan et al., The Incidence of Neurovascular Complications Following Axillary Brachial Plexus Block Using a Transarterial Approach, Regional Anesthesia, 20:486–492 (1995).

S. Winchell et al., The Incidence of Neuropathy Following Upper Extremity Nerve Blocks, Regional Anesthesia, 10:12–15 (1985).

W. Davis et al, Brachial Plexus Anesthesia for Outpatient Surgical Procedures on an Upper Extremity, Mayo. Clin. Proc. 66:470–473 (1991).

D. Moore et al., Bupivacaine: A Review of 11,080 Cases, Anesth. Analg., 57:42–53 (1978).

R. H. De Jong, Axillary Block of the Brachial Plexus, Anesthesiology, 22:215–225 (1960).

J.C. Eisenach, Regional Anesthesia: Vintage Bourdeaux (and Napa Valley), Anesthesiology, 87:467–469 (1997).

L. Brand et al., A Comparison of Supraclavicular and Axillary Techniques for Brachial Plexus Blocks, Anesthesiology, 22:229 (1960).

* cited by examiner

METHOD AND APPARATUS TO DECREASE THE RISK OF INTRANEURONAL INJECTION DURING ADMINISTRATION OF NERVE BLOCK ANESTHESIA

TECHNICAL FIELD

The present invention relates generally to administration of regional or local anesthesia to achieve peripheral nerve blockade, such as is useful when a surgeon operates on a patient's arm or leg or to treat pain emanating in the said or other body parts. More particularly, the present invention relates to an improved method and system of local anesthetic administration that includes a device for indicating pressures interposed between the syringe with local anesthetic and needle for locating the nerves during administration of nerve blocks. Additionally, since the pressure during nerve block injection also depends on the speed of injection, the same device can be used to indirectly monitor and limit the excessive speed of injection.

BACKGROUND OF THE INVENTION

When a surgeon operates on the legs or arms, nerve block anesthesia may be performed to numb or anesthetize the nerves innervating the region being operated upon. Performance of nerve blocks consists of several phases. In the first phase, the operator inserts the needle in the presumed vicinity of the nerve(s) to be blocked. In doing so, the operator may insert the needle "blindly" relying on anatomical landmarks, the operator may try to elicit "paresthesia," whereby the nerve is touched by the needle and the patient perceives "a shock" traveling down the nerve being touched, or the operator may use a nerve stimulator to elicit the motor response (twitch) of the nerve being sought. Whichever method is used, the operator hopes to be in the immediate vicinity to the nerve (which is necessary for reliable nerve blocks) and not in the nerve itself (which may result in traumatic nerve injury when the local anesthetic is injected into the nerve). It is important to emphasize that all three methods used to locate nerves at best approximate the needle position in relationship to the nerve and not confirm it with absolute accuracy. Consequently, with these three described methods for localizing nerves during nerve blocks, the needle tip may inadvertently be inserted into the nerve itself. The resultant injection directly into the nerve(s) may result in significant nerve injury.

Regional anesthesia is widely thought to have a number of advantages over general anesthesia. Regional anesthesia is an effective, low-cost technique that provides a means of selectively anesthetizing a region of the body while minimally interfering with the patient's vital systems. However, one of the major disadvantages of regional anesthesia and nerve blocks in particular is the possibility of nerve damage during administration of nerve blocks or regional anesthesia. Other drawbacks include the risks of systemic and local toxic complications. The primary target for local anesthetic effect in regional anesthesia is neural tissue, such as peripheral nerves, nerve roots, and spinal cord. Thus, it may not be surprising that the most common and troublesome local complications of nerve blocks and regional anesthesia involve the peripheral nerves. Such complications are, fortunately, rare, but they can cause considerable problems for both patient and physician. Of note, even the most careful anesthesiologist will occasionally encounter a PNS complication. For instance, in a survey of hand surgeons regarding experience of neurologic complications associated with axillary block anesthesia, 171 (21%) of the responding 800 surgeons had seen a total of 249 major complications (i.e., lasting at least a year), and 521 (65%) had dealt with minor neurologic sequelae (Stark, "Neurologic Injury from Axillary Block Anesthesia," J. Hand Surg. 21A, 391 (1996)). Thus, about one of five hand surgeons has seen a major neurologic sequela that might have been related to a nerve block. While the overall incidence of nerve damage after nerve blocks is relatively low, the consequences can be catastrophic and result in a temporary or permanent injury to the nerve, loss of limb function and paralysis. See, e.g., Auroy et al., "Serious Complications Related to Regional Anesthesia: Results of a Prospective Survey in France," Anesthesiology, 87, 479–484 (1997); Eisenach, "Regional Anesthesia: Vintage Bordeaux (And Napa Valley)," Anesthesiology, 87, 467–9 (1997). Indeed, the neurologic complications after regional anesthesia are among the most commonly discussed issues at various anesthesia conferences, and a common topic of many scientific publications. Lesions to the brachial plexus seem to be reported most frequently. See, e.g., Bonica et al., "Brachial Plexus Block Anesthesia," Am. J. Surg., 78, 65 (1949); Moberg et al., "Brachial Plexus Block Analgesia with Xylocaine," J. Bone Joint Surg., 33A, 884 (1951); Wolley et al., "Neurological sequelae of brachial plexus nerve block," Ann. Surg., 149, 53 (1959); Brand et al., "A Comparison of Supraclavicular and Axillary Techniques for Brachial Plexus Blocks," Anesthesiology, 22, 226 (1961); Schmidt et al., "Komplikationen und Gefahren der Plexus-brachialis-Anesthesie unter besonderer Berucksictinung von Langzeitschaden," Anasth. Intensivther. Notfallmed., 16, 346 (1981); de Jong, "Axillary block of the brachial plexus," Anesthesiology, 22, 215 (1961); Hamelberg et al., "Perivascular Axillary Versus Supraclavicular Brachial Plexus Block and General Anesthesia," Anesth. Analg., 41, 85 (1962); Wall, "Axillary nerve blocks," Ann. Surg., 149, 53 (1959); Moore et al,. "Bupivacaine: a Review of 11,080 Cases," Anesth. Analg., 57, 42 (1978); Selander et al., "Parasthesiae or No Parasthesiae ? Nerve Lesions after Axillary Blocks," Acta. Anaesth. Scand., 23, 27 (1979); Plevak et al., "Paresthesia Vs. Non Paresthesia—the Axillary Block," Anesthesiology, 59, A216 (1983); Winchell et al., "The incidence of neuropathy following upper extremity nerve blocks," Reg. Anesth., 10, 12 (1985); Tourtier et al., "Complications of Axillary Block Using Two Techniques: Experience with 1400 Cases," Anesthesiology, 71, A726 (1989); Davis et al., "Brachial Plexus Anesthesia for Outpatient Surgical Procedures on an Upper Extremity," Mayo Clin. Proc., 66, 470 (1991); Stan et al., "The Incidence of Neurovascular Complications Following Axillary Brachial Plexus Block Using a Transarterial Approach," Reg. Anesth., 20, 486 (1995); Lofstrom et al., "Late Disturbances in Nerve Function after Block with Local Anesthetic Agents." Acta. Anesth. Scand., 10, 111 (1966); Mogensen et al., "Posttraumatic Instability of the Metacarpophalangeal Joint of the Thumb," Hand, 12, 85(1980).

One of the mechanisms of nerve injury is inadvertent insertion of the needle into a nerve with consequent injection of local anesthetic inside the nerve. This in turn may result in either mechanical trauma to the nerve, ischemic injury to the nerve due the resultant increase in endoneural pressure due to the high pressures inside the nerve, and/or endoneral edema. Indeed, experimentally, it was found that intrafascicular injections in rabbit sciatic nerve in vivo can produce endoneural pressures of more than 700 mm Hg, and after such injections the endoneural pressure could exceed the estimated capillary perfusion pressure for about 15 minutes.

During this period, the nerve fascicle is both ischemic and vulnerable to otherwise toxicologically neutral local anesthetic solutions. Selander et al., "Longitudal Spread of Intraneurally Injected Local Anesthetics," Acta Anesth. Scand., 22, 622 (1978). Similar conditions can also occur in humans, and admixture of epinephrine with local anesthetic can enhance ischemia when injected intraneuronally and thus increase the risk of nerve injury. Selander et al., "Parasthesiae or No Parasthesiae ? Nerve Lesions after Axillary Blocks," Acta Anaesth. Scand., 23, 27 (1979). The pressures on normal injection of local anesthetics in humans range from about 500 mm Hg to about 1200 mm Hg. Higher pressures may indicate an intraneuronal injection. Hadzic et al., "Injection Pressure During Peripheral Nerve Blockade," Anesthesiology, Abstract (2002).

The current recommendations to decrease the risk of intra-neuronal injections consist of slow injection to avoid high injection pressures and the avoidance of injection when high pressures are noticed during injection of local anesthetic. Finucane, *Complications of Regional Anesthesia*, Churchill Livingstone, N.Y. (1999). However, these recommendations assume that the operator or operators are able to perceive the difference between "normal" and "abnormal" injection pressures and take appropriate actions when "abnormal" injection pressures are observed. However, these judgments are prone to subjective interpretation and/or the "feel" of the operators and not on any objective measurements (e.g., measured injection pressure, speed, or similar variables). The ability of different operators to estimate and/or control the injection (especially as with regard to pressure) is further complicated by differences in hand strength and experience among operators as well as differences in resistance to injection for various needle types, lengths, and lumen calibers. In addition, in clinical practice, it is common practice for an operator (e.g., anesthesiologist, nurse anesthesiologist, other anesthesia providers, and the like) to perform the needle placement with an assistant (often without significant experience in nerve blockade) who injects the local anesthetic. This practice poses a risk of exerting too high pressures during injection and possible unrecognized intraneuronal injection. In addition, the operator typically uses both hands to perform the procedure (i.e., place the injection needle in the appropriate location relative to the nerve) and cannot easily determine and/or control the amount of force and pressure that the assistant may employ to inject the local anesthetic.

Moreover, forceful and/or fast injections of local anesthetic solutions can lead to a higher risk of systemic local anesthetic toxicity (e.g., seizures, arrhythmia, cardiovascular collapse, and death) due to tracking of local anesthetic between tissue layers and inadvertent intravascular injections. Additionally, intraneuronal and rapid injections of local anesthetics can backtrack to the spinal column and result in unintended epidural or spinal anesthesia with potentially disastrous consequences (Selander et al., "Longitudal Spread of Intraneurally Injected Local Anesthetics," Acta Anesth. Scand., 22, 622 (1978); Tetzlaff et al., "Subdural Anesthesia as a Complication of an Interscalene Brachial Plexus Block," Regional Anesthesia, 19, 357–359 (1994); Dutton et al., "Total Spinal Anesthesia after Interscalene Blockade of the Brachial Plexus," Anesthesiology, 80, 939–941 (1994)).

Various attempts have been made to improve anesthesia instruments. See, e.g., U.S. Pat. No. 5,119,832 (Jun. 9, 1992); U.S. Pat. No. 5,378,241 (Jan. 3, 1995); U.S. Pat. No. 4,994,036 (Feb. 19, 1991); U.S. Pat. No. 4,775,367 (Oct. 4, 1988); U.S. Pat. No. 4,889,529 (Dec. 26, 1989); U.S. Pat. No. 4,917,670 (Apr. 17, 1990); U.S. Pat. No. 4,917,668 (Apr. 17, 1990); U.S. Pat. No. 5,085,631 (Feb. 4, 1992); U.S. Pat. No. 5,106,376 (Apr. 21, 1992); U.S. Pat. No. 5,135,525 (Aug. 4, 1992); U.S. Pat. No. 5,312,374 (May 17, 1994); U.S. Pat. No. 5,328,479 (Jul. 12, 1994); U.S. Pat. No. 5,512,052 (Apr. 30, 1996); U.S. Pat. No. 5,630,802 (May 20, 1997). None of these attempts, however, focused on controlling and/or measuring the pressure and/or injection speed during injection to avoid an inadvertent intraneuronal injection, or rapid spread, and/or absorption of local anesthetics during nerve blockade/regional anesthesia.

Thus, it is clear that a more objective and reproducible method of monitoring and/or controlling the pressure and/or injection speed during nerve blockage injection, especially by less experienced personnel and/or assistants, would be beneficial in order to decrease the possibility of intraneuronal injection. The present invention provides such a method and apparatus.

SUMMARY OF THE INVENTION

The present invention provides an objective and reproducible method of monitoring and/or controlling the pressure during nerve blockage injection, especially by less experienced personnel and/or assistants, in order to decrease the possibility of intraneuronal injection. More specifically, the present invention employs a pressure sensing and/or limiting device located between an injection device (typically a syringe) and a nerve block needle whereby injection pressure during a nerve block injection can be easily and objectively monitored, thereby allowing the operator to monitor the injection pressure during a nerve blockage injection procedure. Additionally, since the pressure during nerve block injection also depends on the speed of injection, the same device can be used to indirectly monitor and limit excessive injection speeds.

DETAILED DESCRIPTION OF THE INVENTION

The present invention provides an objective and reproducible method of monitoring and/or controlling the pressure during nerve blockage injection, especially by less experienced personnel, in order to decrease the possibility of intraneuronal injection. More specifically, the present invention employs a pressure sensing and/or limiting device located between an injection device (typically a syringe) and a nerve block needle whereby injection pressure during a nerve block injection can be easily and objectively monitored, thereby allowing the operator to monitor the injection pressure during a nerve blockage injection procedure.

For purposes of this invention, the terms "local," "regional," and "nerve block" with respect to anesthesia are intended to be synonymous and interchangeable. For purposes of this invention, a "normal" injection pressure is generally considered to be in the range of the typical pressure normally encountered in a particular type of nerve bock procedure. An "abnormal" injection pressure is generally considered to be above the range of such typical pressures normally encountered in a particular type of nerve block procedure. And, of course, an "intermediate" injection pressure would span the higher end of the "normal" pressure range and the lower end of the "abnormal" range. For guidance purposes only, a normal injection pressure would generally be less than about 15 psi; an intermediate injection pressure generally would be about 15 to about 25 psi; and an abnormal injection pressure would generally be greater than about 25 psi. Of course, these pressures may vary depending on the patient, the type or location of the nerve block, the type, length, or caliber of the needle, the composition, viscosity, or other characteristics of the anesthetic used, speed or force of the injection, as well as other factors.

The present apparatus for performing a nerve block injection comprises an anesthetic delivery device (e.g., syringe) having an anesthetic storage compartment and an output end, an anesthetic needle or catheter having an input end and an output end, an anesthetic passageway connecting the output end of the anesthetic delivery device and the input end of the anesthetic needle whereby anesthetic from the anesthetic storage compartment can be delivered via the output end of the anesthetic needle to a patient, and a pressure sensing device located along, and in pressure sensing communication with, the anesthetic passageway, whereby the pressure of the anesthetic can be monitored during the nerve block injection.

Figures 1, 2:
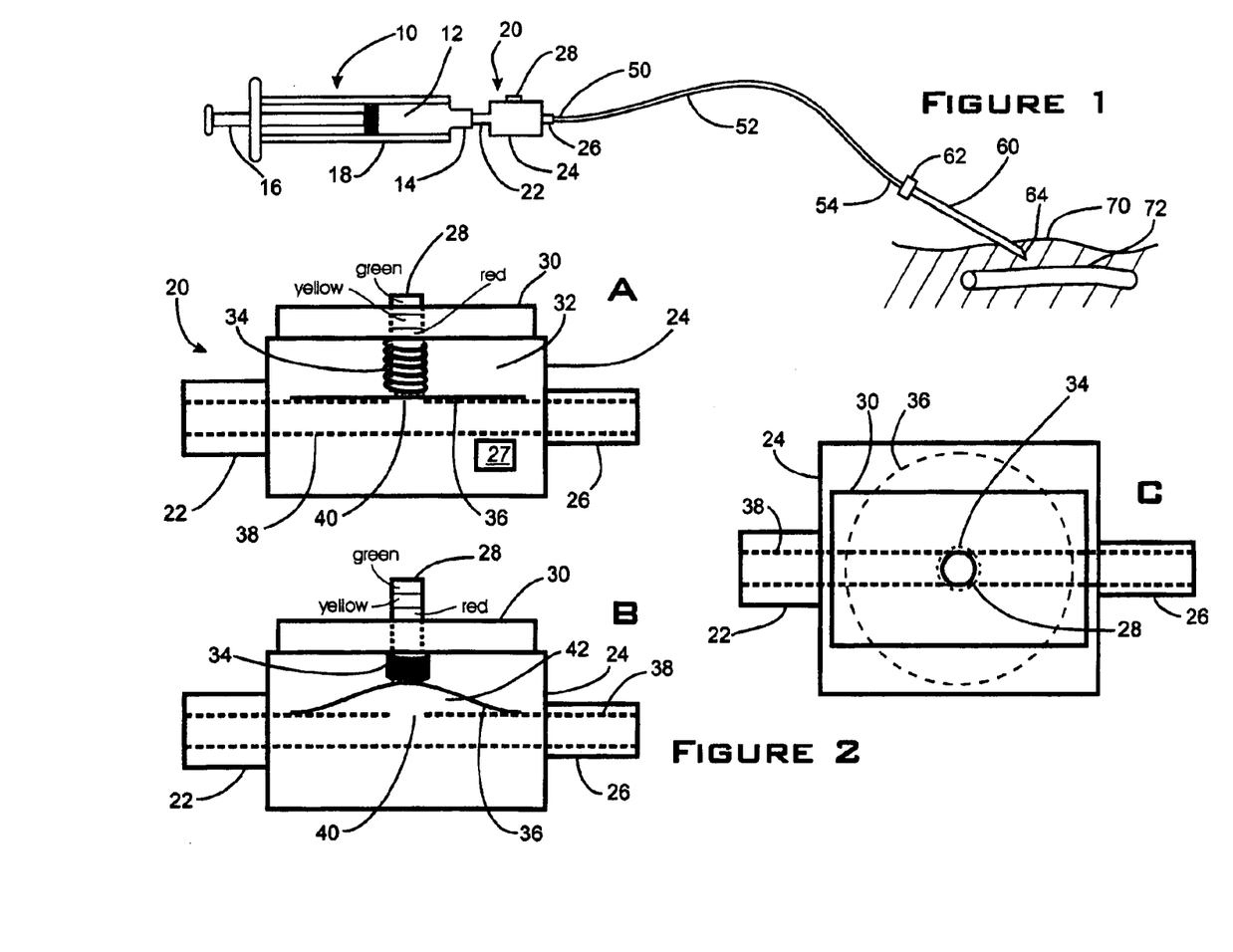
FIG. 1 illustrates one embodiment of the nerve blockage injection system of the present invention.
FIG. 2 illustrates one embodiment of the pressure sensing device used in the present invention. Panel A provides a side view of the pressure sensing device indicating "low" or "normal" pressure. Panel B provides the same side view except that the pressure sensing device indicates "high" or "abnormal" pressure. Panel C provides a top view of the pressure sensing device.

One embodiment of the present invention is shown in FIG. 1 having an anesthetic delivery device 10, a pressure indicating device 20, flexible tubing 52, and a needle 60 for delivering anesthetic adjacent or in the vicinity of nerve 72 for which a nerve block is desired. The anesthetic delivery device 10 shown in FIG. 1 is a syringe having a body 18, an anesthetic storage compartment 12, a movable piston 16, and an output end 14. Other suitable anesthetic delivery devices include, for example, mechanical pumps, and the like so long as they can be controlled by an operator. The output end 14 is adapted to be fitted or attached to the pressure indicating device 20 at its input end 22. The output end 26 is attached via flexible tubing 52 (having an input end 50 and an output end 52). The output end 54 of the flexible tubing 52 is attached to the input end 62 of needle 60. Needle 60 has an output end 64 for delivering anesthetic to a desired location. In operation, as the piston 16 is depressed, anesthetic flows from the anesthetic storage compartment 12, through the pressure indicating device 20 (via passageway 38), through flexible tubing 52, and through needle 60 in order to be injected at the desired location to effect the nerve block.

Although the pressure indicating device 20 shown in FIG. 1 is attached directly to the output end 14 of syringe 10, it could be attached via flexible tubing (similar to flexible tubing 52) so that it could be located anywhere along the length of flexible tubing 52 (including directly attached to the input end 62 of needle 60) as desired. Such a pressure sensing/monitoring device 20 could also be built-in into the syringe-piston mechanism and/or the needle device, rather than being attached to the syringe as shown in FIG. 1. Additionally, more than one pressure indicating device 20 could be included if desired. For example, one pressure indicating device 20 could be located near the output end 14 of syringe 10 and another one near the input end 62 of needle 60 to allow observation of the injection pressure by an operator controlling the needle 60 (e.g., anesthesiologist, nurse anesthesiologist, other anesthesia providers, and the like) and an assistant controlling the syringe 10.

One embodiment of the pressure indicating device 20 is shown in more detail in FIG. 2 wherein the device in Panel A illustrates a normal pressure condition and Panel B illustrates an abnormal or high pressure condition. The pressure indicating device 20 is formed in a body 24 with an input end 22 to receive anesthetic from the anesthetic delivery device 10, a passageway 38 allowing anesthetic to pass through the body 24, and an output end 26 to deliver anesthetic to the needle 60 via flexible tubing 52. The body has an internal flexible membrane 36 within pressure expansion chamber 32 such that as the injection pressure of the anesthetic increase, the membrane 36 can expand within the pressure expansion chamber 32 as shown in Panel B thereby forcing pressure indicating pin 28 to extend beyond a top housing 30 to indicate the injection pressure. As shown in Panel B, the passageway 38 is in fluid communication with the membrane 36 via passageway opening 40. Panels A and B provide side views; Panel C provides a top view. Although membrane 36 is shown as circular in Panel C, it could be of any shape so long as it can be expanded sufficiently to move the pressure indicating pin 28 to indicate increase injection pressure. Preferably, membrane 26 is construction of flexible silicone, flexible polyurethane, flexible rubber, or other flexible materials suitable for use in medical devices.

As the injection pressure increases, anesthetic can force the membrane 36 to expand and thereby enter into portion 42 of the expansion chamber 32 and move the pressure indicating pin 28 upward and out of the top housing 30. With increased pressure, a larger volume of local anesthetic within portion 42 expands or stretches membrane 36 and allows the volume within portion 42 to increase and move the pressure indicating pin 28. The top housing 30 is used to keep the pressure indicating pin 28 in proper alignment so that it can move, depending on the injection pressure, from and to the positions illustrated in Panels A and B. The pressure indicating pin 28 has an associated spring 34 to resist movement upward. The strength of the spring 28 can be selected to provide the desired resistance to movement and, therefore, the range of pressures required to move the pressure indicating pin 28. The extend of expansion of the membrane (and thus the relative size or volume of portion 42 and the extent of travel of pressure indicating pin 28) will depend on the injection pressure and/or injection speed.

As shown in Panels A and B, the pressure indicating pin 28 is color coded to indicate relative injection pressure. In the embodiment indicated, green would indicate normal injection pressure, yellow would indicate an intermediate pressure, and red would indicate an abnormally high pressure. The color exposed on the pressure indicating pin 28 would, therefore, provide a quick and visual indication of the injection pressure along with an indication of how to proceed with the injection. Thus, for example, green (i.e., normal pressure) would indicate continuing the injection procedure; yellow (i.e., intermediate pressure) would indicate the injection could be continued but that the pressure should be monitored carefully; and red (i.e., abnormal pressure) would indicate that the injection should be terminated until the cause of the high pressure is identified. Of course, other color coding or other coding systems can be used if desired so long as the changes in pressure during injection can be easily monitored. In operation, during normal injection pressures, the pressure indicating pin 28 would remain in the retracted position as shown in Panel A with only green showing. During abnormal injection pressure, the pressure indicating pin 28 would move to its extended position as shown in Panel B with red now showing to indicate the abnormal pressure; when the injection pressure decreases, the pressure indicating pin 28 would then move downward, once normal injection pressures are reestablished, to the position shown in Panel A.

Generally, a normal injection pressure (i.e., the green position in FIG. 2) would be less than about 15 psi; an intermediate injection pressure (i.e., the yellow position in FIG. 2) would be about 15 to about 25 psi; and an abnormal injection pressure (i.e., the red position in FIG. 2) would be greater than about 25 psi. Of course, these pressures may vary depending on the patient, the type or location of the nerve block, the type, length, or caliber of the needle, the composition, viscosity, or other characteristics of the anesthetic used, speed or force of the injection, as well as other factors. Thus, pressure indicating devices having different operating pressure ranges may be provided so that the operator can select the appropriate range for the specific application and/or patient.

Generally conventional materials of construction normally used in medical devices can be used to form the pressure indicating device 20. Of course, all materials contacting the anesthetic (e.g., the interior of passageway 38, membrane 36, and portion 42 of expansion chamber 32) should be inert relative to the anesthetic. Additionally, all materials of construction should be capable of being rendered medical sterile using conventional procedures. It is generally preferred, that lightweight plastic materials be used whenever possible. It is also generally preferred that the pressure indicating device 20 is used once and discarded using appropriate procedures. If desired, however, the materials of construction for pressure indicating device 20 can be selected such that it can be resterilized for multiple usage.

In operation, the operator (e.g., anesthesiologist, nurse anesthesiologist, other anesthesia providers, and the like) inserts the needle 60 into the patient through the skin 70 such that the needle tip 64 can deliver anesthetic adjacent, near, or in the immediate vicinity of the nerve 72 to be anesthetized. Conventional techniques are used to position the needle tip 64 in the desired location relative to the nerve 72. Once the needle 60 and needle tip 64 are appropriately placed, the local anesthetic is injected by exerting the pressure on the piston 16 of the syringe 10. The operator or an assistant observes the pressure indicating device 20 during injection so that, if the pressure increases, the appropriate action (as determined by the operator) can be undertaken.

Figure 3:
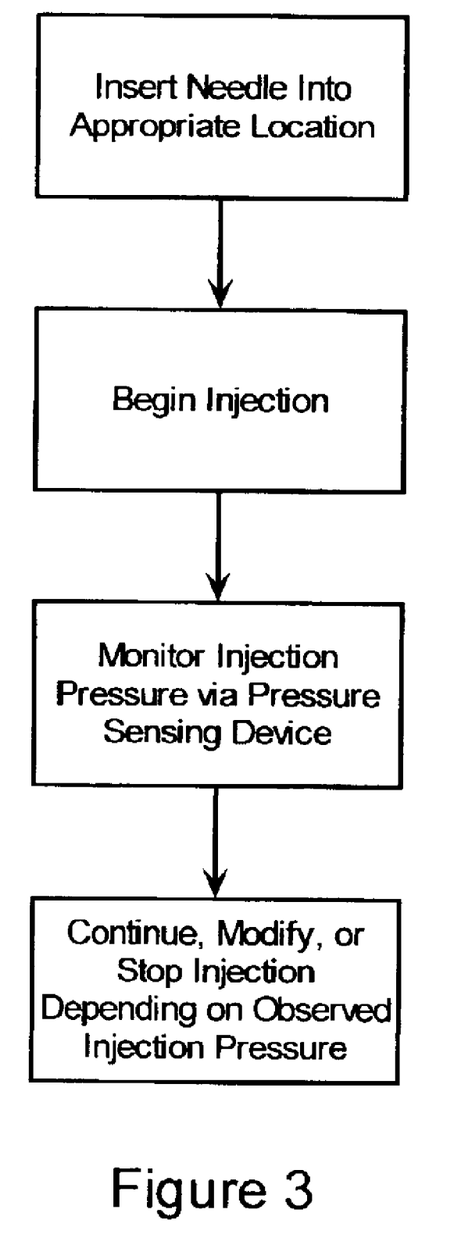
FIG. 3 provides a flowchart illustrate the general method of the present invention.

The general procedure for using the apparatus of the present invention is illustrated in FIG. 3. To begin the nerve block, the nerve block needle is inserted into the patient at the appropriate location (i.e., in the immediate vicinity of the nerve to be blocked). After confirming that the location is acceptable using conventional techniques (e.g., using anatomical landmarks, achieving paresthesia (sensation traveling in the area of the nerve to be blocked), and/or obtaining motor stimulation (muscle twitch) using a nerve stimulator), the injection is begun. The injection pressure during injection is monitored using the pressure sensing device. The injection is continued, modified, or terminated depending on the injection pressure observed. For example, if only normal or acceptable pressures are observed during the injection, the injection is continued until completion. If however, higher than normal pressures are observed, the injection may be modified or terminated as appropriate. The method of the present invention may be carried out by a single individual (e.g., anesthesiologist, nurse anesthesiologist, other anesthesia providers, and the like) or by such an individual using an assistant.

The general procedure for using the apparatus of the present invention is illustrated in FIG. 3. To begin the nerve block, the nerve block needle is inserted into the patent at the appropriate location (i.e., in the immediate vicinity of the nerve to be blocked). After confirming that the location is acceptable using conventional techniques (e.g., using anatomical landmarks, achieving paresthesia (sensation traveling in the area of the nerve to be blocked distribution), and/or obtaining motor stimulation (muscle twitch) using a nerve stimulator), the injection is begun. The injection pressure during injection is monitored using the pressure sensing device. The injection is continued, modified, or terminated depending on the injection pressure observed. For example, if only normal or acceptable pressure are observed during the injection, the injection is continued until completion. If however, higher than normal pressure are observed, the injection may be modified or terminated as appropriate. The method of the present invention may be carried out by a single individual (e.g., anesthesiologist, nurse anesthesiologist, other anesthesia providers, and the like) or by such an individual using an assistant.

Figure 4:
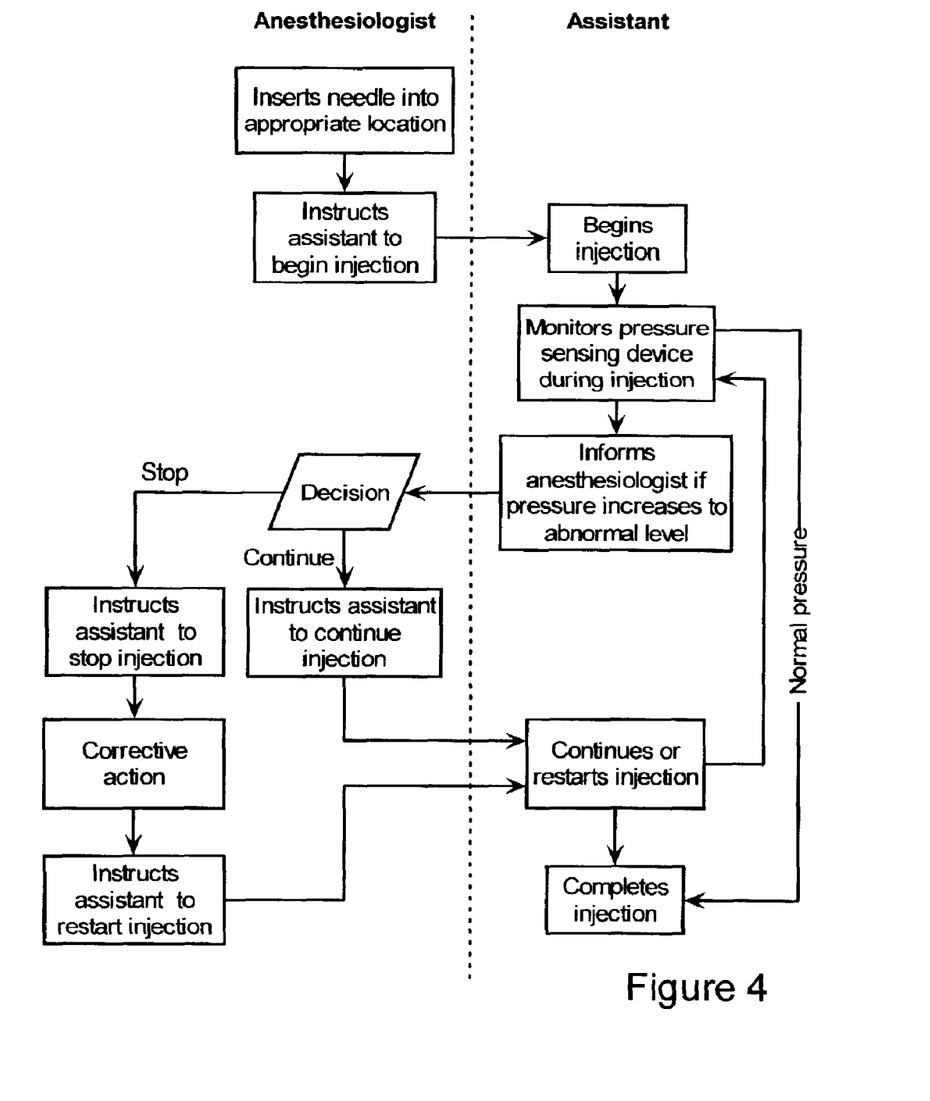
FIG. 4 provides a flowchart illustrating one preferred embodiment of the general method of the present invention wherein an anesthesiologist or other health care provider employs an assistant to operate the injection device.

A preferred procedure for using the apparatus of the present invention is illustrated in FIG. 4 wherein the operator who positions the needle relative to the nerve to be blocked uses an assistant to operate the anesthetic delivery device and observe the pressure indicating device. In FIG. 4, the actions of the anesthesiologist (or other health care provider) and the assistant are generally presented on the left and right sides, respectively. To begin the nerve block, the anesthesiologist inserts the nerve block needle into the patient at the appropriate location (i.e., in the immediate vicinity of the nerve to be blocked). After confirming that the location is acceptable using conventional techniques (e.g., using anatomical landmarks, achieving paresthesia (sensation traveling in the area of the nerve to be blocked), and/or obtaining motor stimulation (muscle twitch) using a nerve stimulator), the anesthesiologist instructs the assistant to begin the injection. The assistant then begins the injection and continuously monitors the pressure sensing device. If only normal or acceptable pressures are observed during the injection, the injection is continued until completion. It, however, intermediate or abnormally high pressures are observed, the assistant informs the anesthesiologist who must make a decision whether to interrupt or continue the injection. If the pressure is only in the intermediate level (i.e., yellow showing on the pressure indicating pin 28 (see FIG. 2)), the anesthesiologist may wish to continue the injection unless abnormal pressures are later observed. Whether in the intermediate or abnormal level, the anesthesiologist may instruct the assistant to stop or interrupt the injection so that corrective action may be undertaken. Such corrective action may include, for example, repositioning the needle relative to the nerve, clearing the needle tip of debris that may have blocked the needle, allowing the pressure to decrease before restarting the injection, reducing the speed of the injection, terminating the injection in order to start over, and the like. Once the anesthesiologist has completed the necessary corrective actions (except, of course, terminating the injection), instructions are given to the assistant to restart the injection. Upon restarting the injection, the assistant will again monitor the injection pressure as described above and provide the necessary information should the pressure increase to intermediate or abnormal levels again.

Although the assistant both monitors the pressure sensing device and operates the syringe or other pumping device in the method illustrated in FIG. 4, the anesthesiologist or other health care provider may also be involved in these activities. For example, the pressure sensing device could be located at a position near the needle (as opposed to near the syringe) to allow the anesthesiologist or other health care provider to easily monitor the injection pressure during injection as well as control the needle position. Alternatively, the anesthesiologist or other health care provider could practice the method of the present invention without the use of an assistant. In such a case, the syringe or other pumping device could preferably be operated by a foot peddle or other device to leave the operator's hand free to place and control the needle.

The present method provides the anesthesiologist the option of continuing the injection even if intermediate or abnormal pressures are observed based on his or her best medical judgement. In such cases, the anesthesiologist will instruct the assistant to continue the injection. Even in such cases, the assistant preferably should continue to monitor the injection pressure in case it increases dramatically so that, if appropriate, the anesthesiologist can reconsider the decision to continue. Generally, high pressures due to a intraneuronal injection are most commonly observed at the beginning of the injection; however, the needle may be initially placed outside the nerve and then inadvertently advanced into the nerve during the injection, resulting in higher pressures.

If desired, the pressure sensing device may also be equipped with a pressure-activated shut-off 27 so that if the injection pressure reaches some predetermined level, flow of the anesthetic will be automatically stopped. Although this predetermined level may be set at any level, it is generally preferred that it be set at a level at or near the abnormal pressure range (e.g., generally at a level of about 25 psi or higher). This automatic shut-off feature may also, if desired, be equipped with a manual override mechanism so that the anesthesiologist, if desired, can continue the injection with or without corrective actions. It will generally be preferred, however, that such an injection not be continued unless such corrective actions are successfully undertaken.

Of course, those skilled in the art may use other, similar mechanisms to measure and/or determine the pressures during nerve block injection and that various details of the invention may be changed without departing from the scope of the invention. All references cited herein are hereby incorporated by reference. Furthermore, the foregoing description is for the purpose of illustration only, and not for the purpose of limitation, which is defined in the following claims.

What is claimed is:

1. A system for administration of a nerve block in a patient with reduced risk of intraneuronal injection, said system comprising
   (1) an anesthetic delivery device having an anesthetic storage compartment and an output end;
   (2) a nerve block needle having an input end and an output end wherein the output end can be inserted into the patient for delivery of anesthetic to the patent in the vicinity of a nerve to be blocked;
   (3) a tube having an anesthetic passageway connecting the output end of the anesthetic delivery device and the input end of the nerve block needle, whereby anesthetic from the anesthetic storage compartment can be delivered via the output end of the nerve block needle to the patient; and
   (4) a pressure sensing device located along, and in pressure sensing communication with, the anesthetic passageway, the pressure sensing device capable of measuring pressures up to about 25 psi, whereby the pressure of the anesthetic can be continuously monitored and controlled during anesthetic delivery to the patient so as to reduce the risk of intraneuronal injection.

2. The system as defined in claim 1, wherein the anesthetic delivery device is a syringe.

3. The system as defined in claim 2, wherein the tube is flexible tubing.

4. The system as defined in claim 3, wherein the pressure sensing device is further equipped with an automatic shut-off device whereby anesthetic delivery is prevented when the pressure of the anesthetic during anesthetic delivery increases above a predetermined level.

5. The system as defined in claim 2, wherein the pressure sensing device allows visual detection of at least normal and abnormal pressures during anesthetic delivery to the patient.

6. The system as defined in claim 1, wherein the tube is flexible tubing.

7. The system as defined in claim 1, wherein the pressure sensing device allows visual detection of at least normal and abnormal pressures during anesthetic delivery to the patient.

8. The system as defined in claim 1, wherein the pressure sensing device is further equipped with an automatic shut-off device whereby anesthetic delivery is prevented when the pressure of the anesthetic during anesthetic delivery increases above a predetermined level.

9. A system for administration of a nerve block in a patient with reduced risk of intraneuronal injection, said system comprising
   (1) a manually operated anesthetic delivery device having an anesthetic storage compartment and an output end;
   (2) a nerve block needle having an input end and an output end wherein the output end can be inserted into the patient for manual delivery of anesthetic to the patent in the vicinity of a nerve to be blocked;
   (3) a tube having an anesthetic passageway connecting the output end of the anesthetic delivery device and the input end of the nerve block needle, whereby anesthetic from the anesthetic storage compartment can be delivered via the output end of the nerve block needle to the patient; and
   (4) a pressure sensing device connected to and in pressure sensing communication with, the anesthetic passageway, the pressure sensing device capable of measuring pressures up to about 25 psi, whereby the pressure of the anesthetic can be continuously monitored and controlled during anesthetic delivery to the patient so as to reduce the risk of intraneuronal injection.

10. The system as defined in claim 9, wherein the pressure sensing device is in a location which allows visible detection of the pressure by an operator of the anesthetic delivery device.

11. The system as defined in claim 10, wherein the anesthetic delivery device is a manually operated syringe.

12. The system as defined in claim 9, wherein the anesthetic delivery device is a manually operated syringe.

* * * * *

UNITED STATES PATENT AND TRADEMARK OFFICE
CERTIFICATE OF CORRECTION

PATENT NO. : 6,866,648 B2
DATED : March 15, 2005
INVENTOR(S) : Admir Hadzic et al.

It is certified that error appears in the above-identified patent and that said Letters Patent is hereby corrected as shown below:

<u>Column 9,</u>
Line 57, after "comprising" insert -- : -- (colon);
Line 62, change "patent" to -- patient --;

<u>Column 10,</u>
Line 36, after "comprising" insert -- : -- (colon);
Line 41, change "patent" to -- patient --;
Line 49, after "to" insert -- , -- (comma).

Signed and Sealed this

Seventh Day of June, 2005

JON W. DUDAS
*Director of the United States Patent and Trademark Office*